United States Patent [19]

Berry

[11] Patent Number: 4,820,266

[45] Date of Patent: Apr. 11, 1989

[54] METHOD OF STOPPING NOSE BLEEDS

[76] Inventor: Yale J. Berry, 134 Clinton Rd., Brookline, Mass. 02100

[21] Appl. No.: 149,159

[22] Filed: Jan. 27, 1988

Related U.S. Application Data

[63] Continuation of Ser. No. 822,940, Jan. 27, 1986, which is a continuation of Ser. No. 611,396, May 18, 1984, abandoned, which is a continuation of Ser. No. 163,160, Jun. 26, 1980, abandoned, which is a continuation of Ser. No. 901,299, May 1, 1978, abandoned.

[51] Int. Cl.$^4$ ............................................. A61M 31/00
[52] U.S. Cl. ........................................ 604/54; 128/325
[58] Field of Search ................ 604/11, 13, 54, 285, 604/286; 128/325

[56] References Cited

U.S. PATENT DOCUMENTS

| | | | |
|---|---|---|---|
| 2,691,985 | 10/1954 | Newsome | 128/325 |
| 2,847,997 | 8/1958 | Tribone | 128/325 |
| 3,049,125 | 8/1962 | Kriwkowitsch | 128/325 |
| 3,342,183 | 9/1967 | Edenbaum | 128/325 |
| 3,349,771 | 10/1967 | Baer | 128/325 |
| 3,420,237 | 1/1969 | Fortay | 128/325 |
| 3,464,413 | 9/1969 | Goldfarb et al. | 128/268 |
| 3,935,859 | 2/1976 | Doyle | 128/342 |
| 4,684,362 | 8/1987 | Holt | 604/54 |

Primary Examiner—C. Fred Rosenbaum
Assistant Examiner—J. L. Kruter
Attorney, Agent, or Firm—Rines and Rines, Shapiro and Shapiro

[57] ABSTRACT

A method of stopping nose bleeds at the Little's area employs a single-piece flattened strip of material that is inserted into a nostril. The strip has sufficient rigidity to permit the strip to be manually inserted by grasping a lower region between the thumb and fingers, has side surface area sufficient to cover the Little's area, and is flexible enough to conform to the shape of the Little's area. The nose is compressed from the outside into direct engagement with the intermediate region of the strip and thereby clamps the strip against the Little's area in direct conforming pressure-applying engagement with the surface network of the Little's area to terminate bleeding of vessels within the network.

5 Claims, 1 Drawing Sheet

METHOD OF STOPPING NOSE BLEEDS

This is a continuation application of Ser. No. 822,940 filed Jan. 27, 1986, which is a continuation application of Ser. No. 611,396 filed May 18, 1984 (abandoned); which is a continuation application of Ser. No. 163,160 filed June 26, 1980 (abandoned); which is a continuation application of Ser. No. 901,299 filed May 1, 1978 (abandoned).

BACKGROUND OF THE INVENTION

The present invention relates to methods of and devices for assisting in the stopping of nose bleeds; being more particularly directed to compressible bandage devices insertible within the nose to stop epistaxis once it has started.

While the medical art is replete with techniques and devices for compressing and/or chemically vasoconstricting ruptured blood vessels, the problem of providing for ready control of nose bleeds, and by the patient himself or herself, still plagues the art. Simple compression of the appropriate blood vessel will stop bleeding provided it can be reached; and if bleeding has stopped for six to nine minutes a small clot will form which may be uncomfortable and otherwise undesireable. Many techniques, moreover, including applying cold to the back of the neck, backwardly depressing the head, stuffing cotton or other absorbing dressings within the nostrils, may acutally be contraindicated for many nosebleeds; and yet, they are almost universally tried and with less than the desired satisfaction.

Examples of topical dressings previously proposed more particularly for other parts of the body are the pressuresensitive dressings of U.S. Pat. Nos. 3,249,109, and 3,342,183, which may include a medicament such as epinephrine, methylaminoaceto-catechol-HCl, or a similar vasoconstrictor; and anti-hemorrhage dressings or pads such as those of U.S. Pat. Nos. 2,024,491, 2,163,588 and 3,386,440. Clamp-type devices or clips for enabling the introduction of an active medical substance to different body parts, including within the nose, have also been proposed as described, for example, in U.S. Pat. Nos. 2,620,795 and 3,788,296.

None of these techniques or devices, however, is applicable to the solution of the problem underlying the present invention which, according to the invention, makes particular use of the largely ignored fact that over ninety percent or more of all nose bleeds occur from the anterior aspect of the nasal septum. More specifically, there is a confluance of blood vessels from the nose and inner nose (and lip) at the so-called Little's area in the interior cartilage septum below the nose bone end. The vessels in the Little's area of the flexible septum are distributed as a surface network of fine, weak arteries; and it is these, and not the larger vessels, that usually rupture and cause most of the nose bleeds.

SUMMARY OF THE INVENTION

An object of the invention, accordingly, is to provide a new and improved method of and device for reliably enabling the constricting of the fine, weak surface blood vessels in the Little's area of the nasal septum, more effectively to contol nose bleeds.

A further object is to provide a novel bandage for stopping epistaxis.

Other and further objects will be explained hereinafter and are more particularly delineated in the appended claims.

In summary, from one of its broader aspects, the invention contemplates a method of stopping nose bleeds at the Little's area of a person's nose, consisting of the following steps: (1) providing a single-piece flattened strip of material that is to be inserted into a nostril of the nose, the strip having an upper end and a lower end and having a predetermined length defined by the distance between said upper end and said lower end, the strip having thickness substantially less than the strip width and having sufficient rigidity to permit said strip to be manually inserted into said nostril lengthwise by grasping a lower region of the strip between the thumb and fingers of a person's hand and using the hand to insert the strip into the nostril, the strip having a region intermediate said upper end and said lower end with side surface area of said intermediate region sufficient to be coextensive with substantially the complete Little's area, and the strip being flexible enough to conform to the shape of Little's area; (2) manually inserting only said strip into said nostril with the strip grasped as aforesaid and using the hand to push the strip lengthwise into said nostril to a position at which said upper end is beyond said Little's area and at which said intermediate region at one side of the strip is placed directly proximal to the adjacent surface network of blood vessels of the Little's area of the nasal septum and said intermediate region extends coextensively over said surface network, with said predetermined length of the strip extending straight from said lower end to said upper end and with the width of the strip extending transversely to said length; (3) and then compressing the nose from the outside into direct engagement with the strip and thereby clamping said strip against said Little's area with said intermediate region of the strip at said one side in direct conforming pressure-applying engagement with said surface network of the Little's area, to terminate bleeding of vessels within said network.

BRIEF DESCRIPTION OF THE DRAWINGS

The invention will now be described with reference to the accompanying drawing.

DETAILED DESCRIPTION OF PREFERRED EMBODIMENTS

Figure 1:
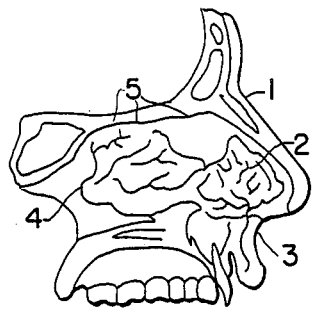
FIG. 1 of which is a cutaway section of the nose region of a human, illustrating the network of fine blood vessels in the Little's area of the nasal septum.

Referring to FIG. 1, the nose 1 is shown cut away to expose the internal vascular anatomy of the cartilage nasal septum, illustrating the before-mentioned fine, weak, surface network of blood vessels 2, known as the Little's area. These fine vessels are fed from larger proximal arteries including the branches of the anterior and posterior ethmoidal arteries 5, the medial branch of the sphenopalatine artery 4, and the septal branch of the superior labial artery 3; and, in more than ninety percent of nose-bleeds, it is the weak vessels in the Little's area that have actually ruptured.

Figure 2:
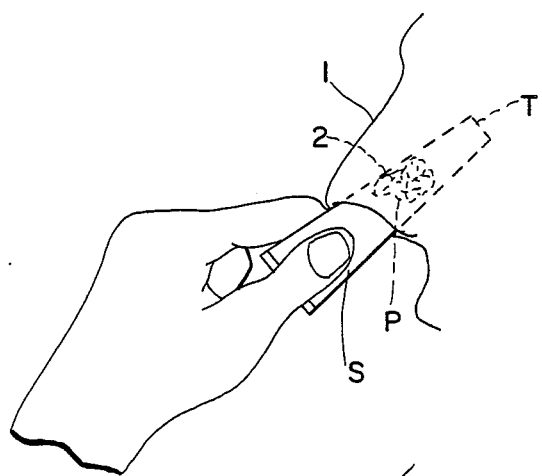
FIG. 2 is a side view illustrating the insertion of a strip constructed in accordance with the invention.

In accordance with the invention, accordingly, concentration is directed to the Little's area for stopping epistaxis once it has started. A small bandage or dressing device in the form of a flattened cotton, felt, paper or flexible plastic pad or similar strip S is designed to have its top portion T inserted within a nostril, as in FIG. 2, and to have its lower portion P below the inserted top T of the strip S of sufficient transverse area to be coextensive with substantially the complete Little's area of vessel network 2.

Figure 3:
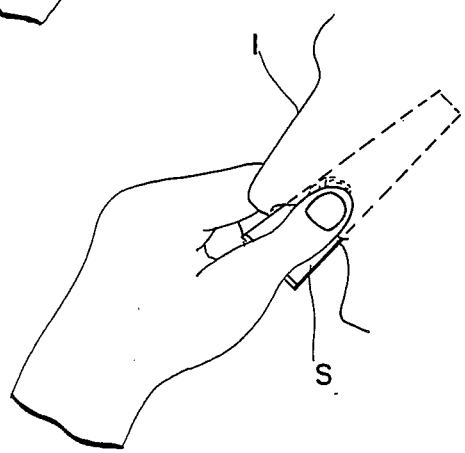
FIG. 3 is a similar view of the operational clamping of the inserted strip to conform to and clamp the said Little's area of the septum.

The strip pad material must be sufficiently flexible to enable its conformance to the surface of the flexible cartilage nasal septum over the Little's area 2, so that, upon external pressure by the thumb and fingers on the sides of the nose, FIG. 3, the portion P may be caused conformably to press against the Little's area network of vessels 2 coextensively with the same and thus to clamp or compress substantially all the little vessels thereof. This has been found extremely successful in effectively stopping most nose bleeds.

In order to provide the appropriate degree of flexibility and conformability and yet sufficient rigidity to enable insertion in the nostril, appropriate lubricant can be applied upon the strip S just before insertion; and, indeed, vasoconstrictor material may be added, as of the previously discussed types.

A successful strip S of this character has been constructed of flattened cotton one and a half centimeters wide, by three centimeters long, and one-half centimeter thick, soaked in an aqueous lubricant such as Lubafax containing a vasoconstrictor in mild concentration (one eigth percent Neo-Synephrine or one quarter percent Ephedrine). Upon clamping or squeezing the nose with the fingers, using the flat of the thumb and the curled portion of the index finger so that the entire soft portion of the tip of the nose is compressed, and holding steadily for about ten minutes, nose bleeds are effectively stopped.

It is possible that bleeding may persist because the strip S is not touching the particular blood vessel which is bleeding, and the bleeding blood vessel is still in the front of the nose. One can tell if one is still bleeding in the following manner. While the nose is compressed, it will be impossible for blood to drip out of the front of the nose. It will, therefore, go down the back of the throat. If the patient can expectorate blood, the bandage has to be adjusted since it is not conforming to the complete Little's area and is not compressing the bleeding vessel thereof. Therefore, the bandage strip may be angled up to the top of the nose as close to the bridge as possible and then again squeezed. If bleeding does not stop after a minute, again as evidenced by blood going down the back of the throat, the strip S should then be placed down to the bottom aspect of the nose and again the nose should be compressed.

If it is impossible to insert the strip S because of a deviated septum and obstruction of the nostril on the side of the bleeding, the strip S may be placed on the opposite side of the septum and compressed as before described. This will provide bulk to compress the broken blood vessel against the nostril itself. It is not as efficient, but works in most instances. Otherwise, the strip S is placed on the side of the bleeding vessel.

Sometimes it is difficult to determine which side is bleeding since blood can go around the back of the nose to the other side. In that instance, the nose should be blown as hard as possible to evacuate all clots. The patient then leans his head forward and determines which side of the nose is bleeding. The bandage is then placed in the nostril on the side of the nasal septum with bleeding.

As before mentioned, an important consideration is that the compressed, flattened cotton or other strip may be stiff if dry. When it becomes moistened with the aqueous lubricant and the vasoconstrictor, it will soften and may be very difficult to place in the nose. This moistening should therefore be applied to the cotton strip immediately before placing it in the nose, but before the lubricant has been allowed to soak into the strip itself. There will thus be enough stiffness and body to allow insertion.

If desired, the strip S may have various geometrical configurations, such as tapering toward the top T; and it may be made in different sizes as for adults and children. Further modifications will occur to those skilled in this art, and such are considered to fall within the spirit and scope of the invention as defined in the appended claims.

What is claimed is:

1. A method of stopping nose bleeds at the Little's area of a person's nose, consisting of the following steps: (1) providing a single-piece flattened strip of material that is to be inserted into a nostril of the nose, the strip having an upper end and a lower end and having a predetermined length defined by the distance between said upper end and said lower end, the strip having thickness substantially less than the strip width and having sufficient rigidity to permit said strip to be manually inserted into said nostril lengthwise by grasping a lower region of the strip between the thumb and fingers of a person's hand and using the hand to insert the strip into the nostril, the strip having a region intermediate said upper end and said lower end with side surface area of said intermediate region sufficient to be coextensive with substantially the complete Little's area, and the strip being flexible enough to conform to the shape of the Little's area; (2) manually inserting only said strip into said nostril with the strip grasped as aforesaid and using the hand to push the strip lengthwise into said nostril to a position at which said upper end is beyond said Little's area and at which said intermediate region at one side of the strip is placed directly proximal to the adjacent surface network of blood vessels of the Little's area of the nasal septum and said intermediate region extends coextensively over said surface network, with said predetermined length of the strip extending straight from said lower end to said upper end and with the width of the strip extending transversely to said length; (3) and then compressing the nose from the outside into direct engagement with the strip and thereby clamping said strip against said Little's area with said intermediate region of the strip at said one side in direct conforming pressure-applying engagement with said surface network of the Little's area, to terminate bleeding of vessels within said network.

2. A method in accordance with claim 1, wherein the step of providing a single-piece flattened strip of material is characterized in that the strip of material is provided with a vasoconstrictor thereon.

3. A method in accordance with claim 1, wherein the step of providing a single-piece flattened strip of material is characterized in that the strip of material is provided with a lubricant thereon.

4. A method of stopping nose bleeds at the Little's area of a person's nose, consisting solely of the following three steps: (1) providing a single-piece flattened strip of material that is to be inserted into a nostril of the nose, the strip having an upper end and a lower end and having a predetermined length defined by the distance between said upper end and said lower end, the strip having thickness substantially less than the strip width and having sufficient rigidity to permit said strip to be manually inserted into said nostril lengthwise by grasping a lower region of the strip between the thumb and fingers of a person's hand and using the hand to insert the strip into the nostril, the strip having a region intermediate said upper end and said lower end with side surface area of said intermediate region sufficient to be coextensive with substantially the complete Little's area, and the strip being flexible enough to conform to the shape of the Little's area; (2) manually inserting only said strip into said nostril with the strip grasped as aforesaid and using the hand to push the strip lengthwise into said nostril to a position at which said upper end is beyond said Little's area and at which said intermediate region at one side of the strip is placed directly proximal to the adjacent surface network of blood vessels of the Little's area of the nasal septum and said intermediate region extends coextensively over said surface network, with said predetermined length of the strip extending straight from said lower end to said upper end and with the width of the strip extending transversely to said length; (3) and then compressing the nose from the outside into direct engagement with the strip and thereby clamping said strip against said Little's area with said intermediate region of the strip at said one side in direct conforming pressureapplying engagement with said surface network of the Little's area, to terminate bleeding of vessels within said network.

5. A method of stopping nose bleeds at the Little's area of a person's nose, consisting solely of the following three steps: (1) providing a device consisting of a single-piece flattened strip of material that is to be inserted into a nostril of the nose, the strip having an upper end and a lower end and having a predetermined length defined by the distance between said upper end and said lower end, the strip having thickness substantially less than the strip width and having sufficient rigidity to permit said strip to be manually inserted into said nostril lengthwise by grasping a lower region of the strip between the thumb and fingers of a person's hand and using the hand to insert the strip into the nostril, the strip having a region intermediate said upper end and said lower end with side surface area of said intermediate region sufficient to be coextensive with substantially the complete Little's area, and the strip being flexible enough to conform to the shape of the Little's area; (2) manually inserting only said device into said nostril with the strip grasped as aforesaid and using the hand to push the strip lengthwise into said nostril to a position at which said upper end is beyond said Little's area and at which said intermediate region at one side of the strip is placed directly proximal to the adjacent surface network of blood vessels of the Little's area of the nasal septum and said intermediate region extends coextensively over said surface network, with said predetermined length of the strip extending straight from said lower end to said upper end and with the width of the strip extending transversely to said length; (3) and then compressing the nose from the outside into direct engagement with the strip and thereby clamping said strip against said Little's area with said intermediate region of the strip at said one side in direct conforming pressure-applying engagement with said surface network of the Little's area, to terminate bleeding of vessels within said network.

* * * * *